(12) United States Patent
Reinehr et al.

(10) Patent No.: US 6,228,127 B1
(45) Date of Patent: *May 8, 2001

(54) BLEACHING OR WASHING COMPOSITION

(75) Inventors: Dieter Reinehr, Kandern (DE); Georges Metzger, Moernach (FR)

(73) Assignee: Ciba Specialty Chemicals Corporation, Tarrytown, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,464

(22) PCT Filed: Oct. 7, 1996

(86) PCT No.: PCT/EP96/04353

§ 371 Date: Apr. 10, 1998

§ 102(e) Date: Apr. 10, 1998

(87) PCT Pub. No.: WO97/14779

PCT Pub. Date: Apr. 24, 1997

(30) Foreign Application Priority Data

Oct. 19, 1995 (GB) .................................................. 9521431
May 8, 1996 (GB) .................................................. 9609549

(51) Int. Cl.$^7$ ................................. C11D 3/39; C07F 15/06

(52) U.S. Cl. .............................. 8/111; 510/311; 510/312; 510/313; 510/314; 510/376

(58) Field of Search ...................................... 510/311, 312, 510/313, 314, 376; 8/111

(56) References Cited

U.S. PATENT DOCUMENTS

| 3,956,211 | 5/1976 | Muto et al. ............................ 260/22 |
| 4,820,439 | * 4/1989 | Rieck .................................... 252/135 |
| 4,973,606 | 11/1990 | Sterzel et al. .......................... 521/27 |

FOREIGN PATENT DOCUMENTS

| 0 392 592 A2 | * 10/1990 | (EP) ............................... C11D/3/39 |
| 0408131 | * 1/1991 | (EP) . |
| 0 408 131 A3 | * 1/1991 | (EP) ............................... C11D/3/39 |
| 0 630 964 A2 | * 12/1994 | (EP) ............................... C11D/3/34 |
| 2291440 | 1/1996 | (GB) . |
| 9530681 | 11/1995 | (WO) . |

* cited by examiner

*Primary Examiner*—Yogendra Gupta
*Assistant Examiner*—Brian P. Mruk
(74) *Attorney, Agent, or Firm*—Kevin T. Mansfield

(57) ABSTRACT

A bleaching or washing composition comprising a peroxy compound and a specified cobalt compound is disclosed, as well as a process for bleaching or washing a fabric or dishes by contacting them with said bleaching or washing composition.

44 Claims, No Drawings

BLEACHING OR WASHING COMPOSITION

The present invention relates to bleaching or washing compositions comprising a peroxygen compound and, as bleach activator, a cobalt compound.

Bleaching or washing compositions which contain a peroxide bleaching agent are well-known. In such compositions, the bleaching agent functions to remove such common domestic stains as tea, coffee, fruit starch and wine stains from e.g. clothing or dishes by washing the soiled clothing or dishes in the presence of the bleaching agent at the boil. If the washing temperature is reduced to below 60° C., however, the efficacy of the the bleaching agent is correspondingly reduced.

It is also well-known that certain heavy metals, or complexes thereof, function to catalyze the decomposition of hydrogen peroxide, or of compounds which are capable of liberating hydrogen peroxide, in order to render the peroxide compound effective at temperatures below 60° C.

For example, in U.S. Pat. No. 5,114,511, there is described the activation of a peroxy compound by a complex formed from a transition metal (Mn, Co, Fe or Cu) and a non-(macro)cyclic ligand, preferably 2,2-bispyridylamine or 2,2-bispyridylmethane.

Moreover, in EP-B 408 131, a bleaching composition is disclosed comprising a peroxy compound and, as catalyst for the bleaching action of the said peroxy compound, a cobalt complex of a ligand derived from a specified o-hydroxy-benzaldehyde, e.g. 5-methyl isophthalaldehyde, and a specified alkylenediamine, e.g.1,3-diaminopropane.

It has now been found that certain other cobalt compounds are also excellent bleach catalysts for peroxy compounds and, surprisingly, relative to known bleach catalysts, provide enhanced bleach effects.

Accordingly, the present invention provides a bleaching or washing composition comprising a) a peroxy compound; and b) 0.0005 to 0.5, preferably 0.005 to 0.05%, by weight of cobalt, of a cobalt compound having one of the formulae:

(1)

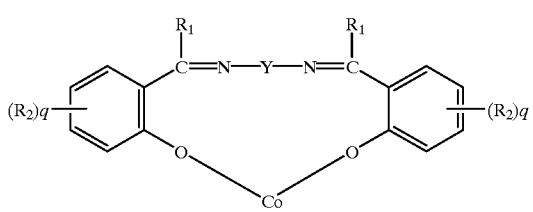

(2)

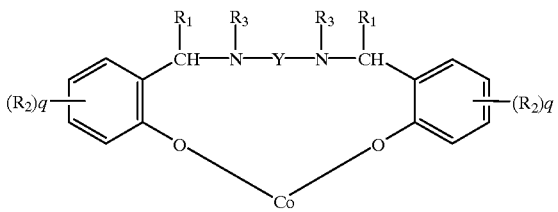

(3)

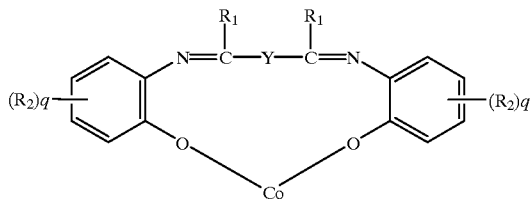

(4)

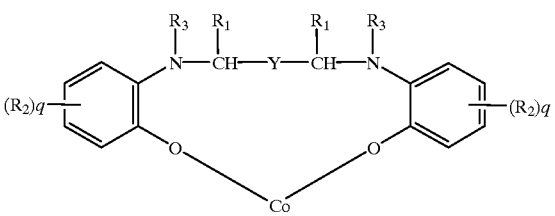

(5)

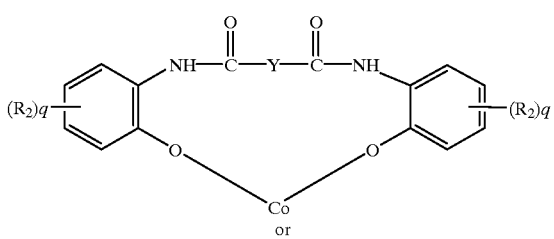

or (6)

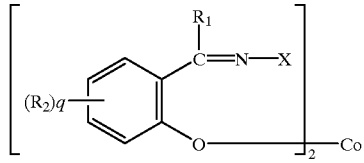

in which $R_1$ is hydrogen, alkyl, cycloalkyl or aryl; $R_2$ is hydrogen, alkyl, alkoxy, halogen, cyano, NH(alkyl), N(alkyl)$_2$, N$^{\oplus}$(alkyl)$_3$, SO$_3$M, COOM or hydroxy; $R_3$ is hydrogen or alkyl; Y is a direct bond, alkylene, cyclohexylene, o-, m- or p-phenylene, C(C=O)—(C=O) or Y is a residue having one of the formulae:

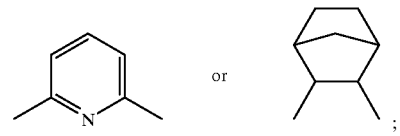

X is alkyl, —CH$_2$COOC$_1$–C$_4$alkyl, aryl, —NH—phenyl, hydroxy, amino or —NH—C(=O)—NH$_2$; M is hydrogen, an alkali metal atom, ammonium or a cation formed from an amine; and q is 0,1, 2 or 3, provided that when, in the compounds of formula (1), Y is alkylene, then q is 1, 2 or 3 and $R_2$ is preferably SO$_3$M.

When one or more of $R_1$, $R_2$, $R_3$ and X, or a component of $R_1$, $R_2$ and X are alkyl, preferred alkyl groups are C$_1$–C$_{12}$, especially C$_1$–C$_4$alkyl groups. The alkyl groups may be unbranched or branched.

Alkoxy groups $R_2$ are preferably C$_1$–C$_8$-, especially C$_1$–C$_4$-alkoxy groups. The alkoxy groups may be unbranched or branched.

Halogen atoms $R_2$ are preferably bromo or, especially, chloro atoms.

$N$(optionally substituted alkyl)$_2$ groups $R_2$ are preferably $N$(optionally substituted $C_1$–$C_4$alkyl)$_2$ groups, especially $N$(methyl)$_2$ or $N$(ethyl)$_2$.

$N^{\oplus}$(optionally substituted alkyl)$_3$ groups $R_2$ are preferably $N^{\oplus}$(optionally substituted $C_1$–$C_4$alkyl)$_3$, especially $N^{\oplus}$(methyl)$_3$ or $N^{\oplus}$(ethyl)$_3$.

When $R_1$ is cycloalkyl, it is preferably cyclopentyl or cyclohexyl.

When $R_1$ is aryl, it is preferably a phenyl or naphthyl group. Any aryl group $R_1$ or X, or any aryl group which is a component of a group Y may be substituted e.g. by $C_1$–$C_4$alkyl, such as methyl, ethyl, propyl, isopropyl, butyl, isobutyl, sec.-butyl or tert.-butyl, by $C_1$–$C_4$-alkoxy such as methoxy, ethoxy, propoxy, isopropoxy, butoxy, isobutoxy, sec.-butoxy or tert.-butoxy, by halogen such as fluorine, chlorine or bromine, by $C_2$–$C_5$-alkanoyl, by benzoyl, by $C_2$–$C_5$-alkanoylamino, such as acetylamino, propionylamino or butyrylamino, by nitro, $SO_3M$, $CO_2M$, in which M has its previous significance, or by di-$C_1$–$C_4$alkyl amino.

When Y is unsubstituted alkylene, it is preferably a $C_2$–$C_4$-alkylene residue, especially a —$CH_2$—$CH_2$— bridge. Y may also be a $C_2$–$C_8$-alkylene residue which is interrupted by oxygen or, especially, by nitrogen, preferably —$(CH_2)_m$—NH—$(CH_2)_m$— in which m is 2, 3, 4 or 5, in particular the —$(CH_2)_3$—NH—$(CH_2)_3$—, —$(CH_2)_2$—NH—$(CH_2)_2$ or —$(CH_2)_2$—N($CH_3$)—$(CH_2)_2$— bridge. Y may also be a $C_2$–$C_8$-alkylene residue which is substituted or interrupted by one or more aryl or arylene groups, especially phenyl or phenylene groups. Examples of preferred groups Y of this type include groups having the formula:

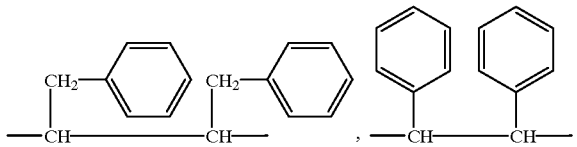

—$CH_2$-(o-, m- or p-)phenylene-$CH_2$—.

With respect to the compounds of formula (1), preferably each $R_1$ is hydrogen, $R_2$ is hydrogen, OH or $SO_3M$ in which M has its previous significance and is preferably Na, q is 1 and Y is unsubstituted $C_2$–$C_4$-alkylene, $C_2$–$C_8$-alkylene interrupted by NH, $C_2$–$C_8$-alkylene interrupted or substituted by optionally substituted o-, m- or p-phenylene, or Y is optionally substituted o-, m- or p-phenylene.

In relation to the compounds of formula (2) or (4), preferably each $R_1$ is hydrogen, $R_2$ is hydrogen, OH or $SO_3M$ in which M has its previous significance and is preferably Na, $R_3$ is hydrogen, q is 0 or 1 and Y is $C_2$–$C_8$-alkylene interrupted by NH.

With regard to the compounds of formula (3), preferably each $R_1$ is hydrogen, $R_2$ is hydrogen, OH or $SO_3M$ in which M has its previous significance and is preferably Na, q is 0 or 1 and Y is $C_2$–$C_8$-alkylene interrupted by NH.

In relation to the compounds of formula (5), preferably each $R_2$ is hydrogen, OH or $SO_3M$ in which M has its previous significance and is preferably Na, q is 0 or 1 and Y is a direct bond.

With respect to the compounds of formula (6), preferred compounds are those in which each $R_1$ is hydrogen, $R_2$ is hydrogen, OH or $SO_3M$ in which M has its previous significance and is preferably Na, q is 1 and X is OH.

In each of the compounds of formula (1) to (6), it is preferred that they are used in neutral form, i.e. that M, when present, is other than hydrogen, preferably a cation formed from an alkali metal, in particular sodium, or from an amine.

The cobalt compounds of formulae (1) to (6) are believed to be new compounds and, as such, form a further aspect of the present invention. The compounds of formula (1) to (6) may be produced by known methods, e.g. by the methods analogous to those disclosed in U.S. Pat. No. 4,655,785 relating to similar copper compounds.

The peroxy component a) of the fabric bleaching compositions of the present invention may be hydrogen peroxide, a compound which liberates hydrogen peroxide, a peroxyacid, a peroxyacid bleach precursor or a mixture thereof.

Compounds which liberate hydrogen peroxide are well known and include, e.g., inorganic compounds such as alkali metal peroxides, -perborates, -percarbonates, -perphosphates and -persulfates and organic compounds such as peroxylauric acid, peroxybenzoic acid, 1,12-diperoxydodecanoic acid, diperoxyisophthalic acid and urea peroxide, as well as mixtures thereof. Sodium percarbonate and sodium perborate, in particular sodium perborate monohydrate, are preferred.

Peroxyacid compounds and peroxyacid bleach precursors are also well known and a summary of references describing them is provided in the above-mentioned U.S. Pat. No. 5,114,606.

Examples of peroxyacid bleach precursors include
benz(4H)-1,3-oxazin-4-one derivatives, especially substituted 2-phenyl-benz(4H)-1,3-oxazin-4-one
2-(N,N,N-trimethyl ammonium)ethyl sodium-4-sulfophenyl carbonate chloride (SPCC)
N-octyl,N,N-dimethyl-N10-carbophenoxy decyl ammonium chloride (ODC)
3-(N,N,N-trimethyl ammonium)propyl sodium 4-sulfophenyl carboxylate
N,N,N-trimethyl ammonium toluyloxy benzene sulfonate
sodium-4-benzoyloxy benzene sulfonate (SBOBS)
N,N,N',N'-tetraacetyl ethylene diamine (TAED)
sodium-1-methyl-2-benzoyloxy benzene-4-sulfonate
sodium-4-methyl-3-benzoyloxy benzoate and
sodium nonanoyloxybenzene sulfonate (NOBS).

The substituted 2-phenyl-benz(4H)-1,3-oxazin-4-one, NOBS and TAED precursors are preferred.

Preferably, the amount of the peroxy compound in the bleaching or washing composition according to the invention ranges from 0.5 to 50%, especially from 2 to 20% by weight, based on the total weight of the composition.

When the bleaching or washing composition of the present invention is a fabric bleaching composition, it preferably also comprises a surfactant and a detergent builder component.

The surfactant component is preferably an anionic surfactant, a nonionic surfactant or a mixture thereof and is preferably present in an amount of 5 to 50%, especially 5 to 25% by weight, based on the total weight of the fabric bleaching composition.

The anionic surfactant component may be, e.g., a sulphate, sulphonate or carboxylate surfactant, or a mixture of these.

Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula R—CO(R$^1$)CH$_2$COOM$^1$ in which R is alkyl or alkenyl having 9–17 carbon atoms in the alkyl or alkenyl radical, R$^1$ is C$_1$–C$_4$ alkyl and M$^1$ is alkali metal.

The nonionic surfactant component may be, e.g., a condensate of ethylene oxide with a C$_9$–C$_{15}$ primary alcohol having 3–8 moles of ethylene oxide per mole.

The detergent builder component is preferably present in an amount of 5 to 80%, especially 10 to 60% by weight, based on the total weight of the fabric bleaching composition. It may be an alkali metal phosphate, especially a tripolyphosphate; a carbonate or bicarbonate, especially the sodium salts thereof; a silicate; an aluminosilicate; a polycarboxylate; a polycarboxylic acid; an organic phosphonate; or an aminoalkylene poly(alkylene phosphonate); or a mixture of these.

Preferred silicates are crystalline layered sodium silicates of the formula NaHSi$_m$O$_{2m+1}$·pH$_2$O or Na$_2$Si$_m$O$_{2m+1}$·pH$_2$O in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

The bleaching or washing compositions of the invention preferably also contain one or more agents capable of binding cobalt, in particular an aminocarboxylate, an aminophosphonate, a polyamine or a mixture of these. Examples of aminocarboxylates include ethylenediaminetetraacetate, N-hydroxyethylenediaminetriacetate, nitrilotriacetate, ethylenediaminetetrapropionate, triethylenetetraaminehexaacetate, diethylenetriaminepentaacetate, ethylenediaminedisuccinate, especially the S,S isomer, and ethanoldiglycine, each in their acid forms or as the respective alkali metal, ammonium or substituted ammonium salts, as well as mixtures thereof. Examples of aminophosphonates include diethylenetriaminepentamethylene phosphonic acid and salts thereof. Examples of polyamines are, e.g., diethylenetriamine, pentamethyidiethylenetriamine, 1,1',7,7'-tetramethyl-4-hydroxymethyl-diethylenetriamine and 1,4,4'-trimethyl-1'-hydroxymethyl-ethylenediamine. Most preferred agents capable of binding cobalt are diethylenetriaminepentamethylene phosphonic acid, diethylenetriaminepentaacetic acid, triethylenetetraaminehexaacetic acid and salts thereof, and diethylenetriamine.

The agent capable of binding cobalt is generally present in an amount of 0.1 to 10%, preferably from 0.1 to 3% by weight, based on the weight of the bleaching or washing composition.

The presence of the agent capable of binding cobalt in the bleaching and washing compositions of the invention has the desired effect of reducing any fabric damage which may be caused by the use of the cobalt compounds of formula (1) to (6).

When the bleaching or washing composition of the present invention is a dishwashing composition, it preferably comprises, in addition to components a) and b), a detergent builder component, preferred examples of which are those indicated hereinbefore in relation to the fabric bleaching or washing composition of the present invention; and a buffering agent.

Preferred dishwashing compositions of the present invention, however, will be essentially free from phosphates so that their preferred builder component will be, e.g., sodium citrate, sodium carbonate, calcium carbonate, a zeolite or any mixture of these materials.

The dishwashing compositions of the present invention preferably contain 0.1 to 10%, more preferably 0.5 to 5% by weight of a low- to non-foaming nonionic surfactant, in order to improve the detergency of the compositions and to suppress excessive foaming due to any protein soil. Examples of suitable low- to non-foaming nonionic surfactants are condensates of ethylene oxide with a C$_9$–C$_{15}$ primary alcohol having 3–8 moles of ethylene oxide per mole.

Preferably, the dishwashing compositions of the present invention comprise from 5 to 60% by weight of a detergent builder component; and from 5 to 75% by weight of a buffering agent, preferably an alkali metal carbonate, bicarbonate, borate or silicate, especially a sodium silicate having an Na$_2$O:SiO$_2$ ratio in the range of from 2:1 to 1:4, especially from 1:1.8 to 1:2.5.

The bleaching or washing compositions of the invention may contain, in addition to the components already mentioned, and depending on whether they are intended for fabric bleach or for dishwashing application, one or more polymers known to be useful in preventing the transfer of labile dyes between fabrics during the washing cycle; fluorescent whitening agents, such as a bis-triazinylamino-stilbene-disulphonic acid, a bis-triazolyl-stilbene-disulphonic acid, a bis-styryl-biphenyl, a bis-benzofuranylbiphenyl, a bis-benzoxalyl derivative, a bis-benzimidazolyl derivative, a coumarine derivative or a pyrazoline derivative; soil suspending agents, for example sodium carboxymethylcellulose; salts for adjusting the pH, for example alkali or alkaline earth metal silicates; foam regulators, for example soap; anti-scale agents such as phosphonates, especially ethylenediamine tetra-(methylene phosphonate), diethylenetriamine penta-(methylene phosphonate) or ethylene hydroxy diphosphonate, polyacrylates, polymaleates or copolymers thereof having molecular weights of up to 6000, or polypeptides; clays such as hectorites or montmorillonite which are effective in reducing spot formation on glassware; salts for adjusting the spray drying and granulating properties, for example sodium sulphate; perfumes; and also, if appropriate, antistatic and softening agents such as smectite clays; enzymes, such as proteases (examples of which are described, e.g., in EP-A-0 530 870), cellulases, lipases, oxidases and amylases; photobleaching agents; pigments; and/or shading agents. These constituents should, of course, be stable to the bleaching system employed.

A particularly preferred fabric bleaching composition co-additive is a polymer known to be useful in preventing the transfer of labile dyes between fabrics during the washing cycle. Preferred examples of such polymers are polyvinyl pyrrolidones, optionally modified by the inclusion of an anionic or cationic substituent, especially those having a molecular weight in the range from 5000 to 60,000, in particular from 10,00 to 50,000. Preferably, such polymer is used in an amount ranging from 0.05 to 5%, preferably 0.2–1.7% by weight, based on the weight of the detergent.

The formulation of the bleaching or washing compositions of the invention may be conducted by any conventional technique.

The bleaching or washing composition may be formulated as a solid; or, in the case of a fabric bleaching composition, as a non-aqueous liquid fabric bleaching composition, containing not more than 5, preferably 0–1 wt. % of water, and based on a suspension of a builder in a non-ionic surfactant, as described, e.g., in GB-A-2158454.

Preferably, the bleaching or washing composition is in powder or granulate form.

Such powder or granulate forms may be produced by firstly forming a base powder by spray-drying an aqueous slurry containing all the said components, apart from the components a) and b); then adding the components a) and b) by dry-blending them into the base powder. In a further process, the component b) may be added to an aqueous slurry containing the surfactant and builder components, followed by spray-drying the slurry prior to dry-blending component a) into the mixture. In a still further process, a nonionic component is not present, or is only partly present in an aqueous slurry containing anionic surfactant and builder components; component b) is incorporated into the nonionic surfactant component, which is then added to the spray-dried base powder; and finally component a) is dry-blended into the mixture.

The present invention also comprises a bleaching or washing process comprising contacting a fabric or dishes to be bleached or washed with an effective amount of a fabric bleaching or dishwashing composition according to the present invention. Preferably the amount of the bleaching or washing composition used is such that the amount of cobalt complex b) provides from 0.001 to 100 ppm, preferably from 0.01 to 20 ppm of cobalt in the bleaching or washing bath.

The following Examples serve to illustrate the invention; parts and percentages are by weight, unless otherwise stated.

EXAMPLE 1

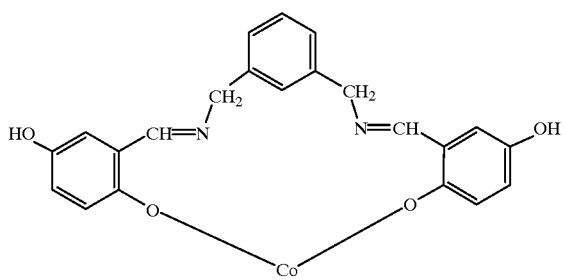
(101)

A) 1.35 g. of α,α'-diamino-m-xylene are added to a solution of 2.76 g. of 2,5-dihydroxybenzaldehyde in 40 ml. of ethanol at 20° C. whereupon a yellow solution is produced. This solution is stirred at 90° C. for 30 minutes, whereupon an orange-yellow precipitate is formed. After filtering of the precipitate at 20° C., there are obtained 3.03 g. (80% theory) of an orange crystalline product having the formula:

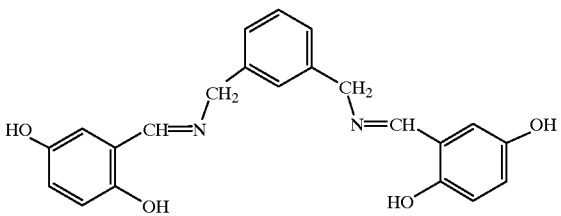
(101a)

Elemental analysis of the compound of formula (101a) and having the empirical formula $C_{22}H_{20}N_2O_4$ gives:
Required %: C 70.20; H 5.36; N 7.44; 0 17.00.
Found %: C 70.07; H 5.45; N 7.38; 0 17.1.

B) 0.9 g. of Co(II) acetate is added to a solution of 1.35 g. of the compound of formula (101a) in 30 ml. of water and the mixture so obtained is stirred at 80° C. for 30 minutes. A precipitate is formed which is filtered off to give 1.7 g.(100% theory) of the compound of formula (101) as a dark brown powder.

Elemental analysis of the compound of formula (101) and having the empirical formula $C_{22}H_{18}N_2O_4Co \cdot 3H_2O$ gives:
Required %: C 54.2; H 4.96; N 5.74; Co 12.09.
Found %: C 53.19; H 4.84; N 5.58; Co 12.50.

EXAMPLE 2

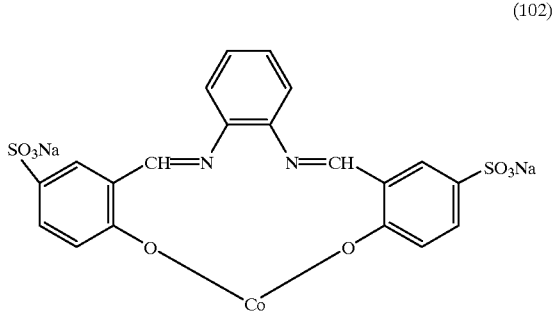
(102)

A) A solution of 2.65 g. of cobalt (II) chloride in 20 ml. of water is added to a solution of 10.6 g. of the di-sodium salt of 5-sulfo-salicylaldehyde in 50 ml. of water. The mixture so obtained is stirred for 3 hours under reflux and then cooled to 20° C. The product which precipitates has the formula:

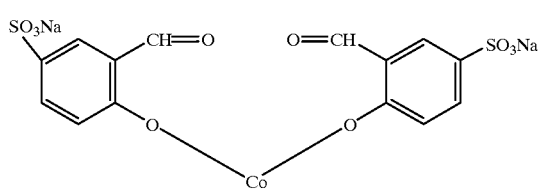
(102a)

After filtering off and drying the product, there are obtained 9.3 g. (79.2% theory) of the compound of formula (102a) as a dark-yellow compound.

Elemental analysis of the compound of formula (102a) and having the empirical formula $C_{14}H_8S_2O_{10}Na_2Co \cdot 4H_2O$ gives:
Required %: C 28.63; H 2.75; S 10.92; Co 10.04.
Found %: C 28.48; H 2.83; S 11.06; Co 10.4.

B) 0.54 g. of 1,2-diaminobenzene is added to a solution of 2.89 g. of the compound of formula (102a) in 25 ml. of water and the mixture is stirred at 80° C. for 2 hours. The reaction mixture is then diluted with 150 ml. of ethanol, cooled and filtered. There are obtained 3.0 g. (83.2% theory) of a dark brown powder having the formula (102).

Elemental analysis of the compound of formula (102) and having the empirical formula $C_{20}H_{12}N_2S_2O_8Na_2Co \cdot 8H_2O$ gives:

Required %: C 33.23; H 3.93; N 3.87; S 8.87; Co 8.15; $H_2O$ 20.14.

Found %: C 33.36; H 3.91; N 4.13; S 8.51; Co 8.6; $H_2O$ 20.14.

EXAMPLE 3

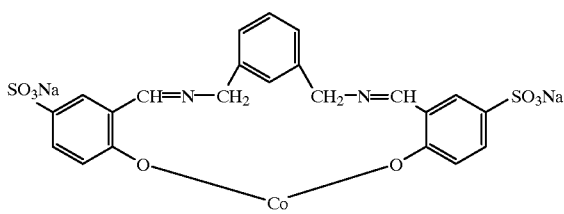

(103)

0.725 g. of α,α'-diamino-m-xylene is added to a solution of 2.89 g. of the compound of formula (102a), as described in Example 2, in 25 mi. of water. The mixture is heated to 80° C. and stirred for 2 hours at this temperature. After cooling to 20° C., the mixture is diluted with 150 ml. ethanol and filtered off. There are obtained 3.32 g. (88% theory) of the dark brown product of formula (1 03).

Elemental analysis of the compound of formula (103) and having the empirical formula $C_{22}H_{16}N_2S_2O_8Na_2Co$ gives:

Required %: C 35.00; H 4.35; N 3.71; S 8.49; Co 7.81; $H_2O$ 19.81.

Found %: C 35.44; H 4.36; N 3.77; S 8.37; Co 7.56; $H_2O$ 19.81.

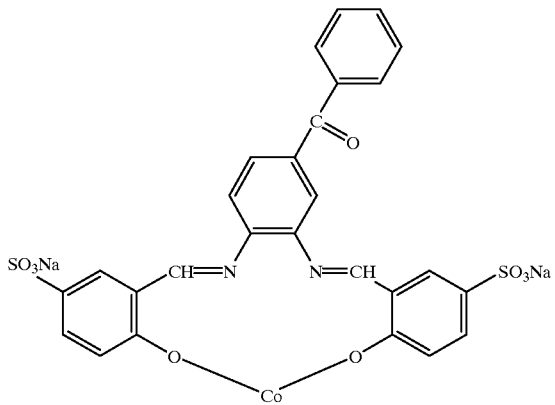

(104)

EXAMPLE 4

The procedure described in Example 2(B) is repeated except that 3,4-diaminobenzophenone is used instead of 1,2-diaminobenzene. In this way, the compound of formula (104) is obtained as a dark brown powder in a yield of 73% of theory.

Elemental analysis of the compound of formula (104) and having the empirical formula $C_{27}H_{16}N_2S_2O_9Na_2Co \cdot 8 H_2O$ gives:

Required %: C 39.39; H 3.89; N 3.40; S 7.79; Co 7.16; $H_2O$ 17.22.

Found %: C 39.59; H 3.79; N 3.37; S 7.81; Co 8.0; $H_2O$ 17.22.

EXAMPLE 5

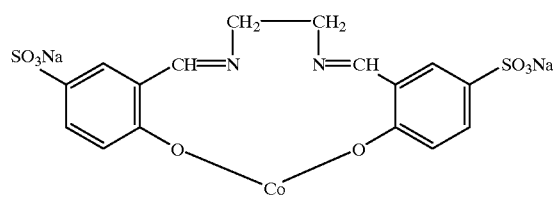

(105)

The procedure described in Example 2(B) is repeated except that ethylenediamine is used instead of 1,2-diaminobenzene. In this way, the compound of formula (105) is obtained in a comparable yield.

Elemental analysis of the compound of formula (105) and having the empirical formula $C_{16}H_{12}N_2O_8S_2Na_2Co \cdot 8.34\ H_2O$ gives:

Required %: C 28.28; H 4.25; N 4.12; S 9.44; Co 8.67; $H_2O$ 22.11.

Found %: C 28.30; H 4.44; N 4.70; S 9.10; Co 8.45; $H_2O$ 22.10.

EXAMPLE 6

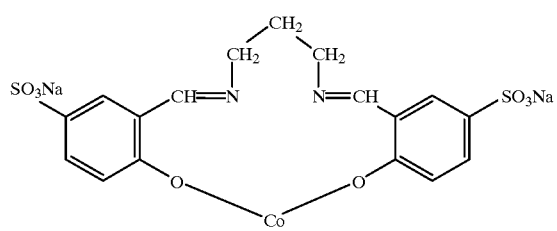

(106)

The procedure described in Example 2(B) is repeated except that 1,3-diaminopropane is used instead of 1,2-diaminobenzene. In this way, the compound of formula (106) is obtained in a comparable yield.

Elemental analysis of the compound of formula (106) and having the empirical formula $C_{17}H_{14}O_8N_2S_2Na_2Co \cdot 8.34\ H_2O$ gives:

Required %: C 30.88; H 4.13; N 4.24; S 9.70; Co 8.91; $H_2O$ 17.82.

Found %: C 30.43; H 4.25; N 4.20; S 9.25; Co 9.43; $H_2O$ 17.83.

EXAMPLE 7

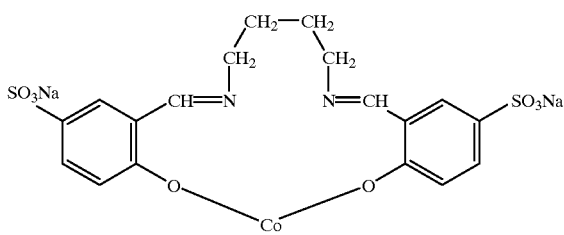
(107)

The procedure described in Example 2(B) is repeated except that 1,4-diaminobutane is used instead of 1,2-diaminobenzene. In this way, the compound of formula (107) is obtained in a comparable yield.

Elemental analysis of the compound of formula (107) and having the empirical formula $C_{18}H_{16}N_2O_8S_2Na_2Co \cdot 6.87\,H_2O$ gives:

Required %: C 31.74; H 4.40; N 4.11; S 9.42; Co 8.65; $H_2O$ 18.17.

Found %: C 31.08; H 4.39; N 4.12; S 9.25; Co 9.16; $H_2O$ 18.17.

EXAMPLES 8 to 17

A standard (ECE) washing powder is made up from the following components in the indicated proportions:
8.0% Sodium ($C_{11.5}$)alkylbenzenesulphonate;
2.9% Tallow-alcohol-tetradecane-ethyleneglycolether(14 moles EO);
3.5% Sodium soap;
43.8% Sodium triphosphate;
7.5% Sodium silicate;
1.9% Magnesium silicate;
1.2% Carboxymethylcellulose;
0.2% EDTA;
21.2% Sodium sulphate; and
9.8% Water.

An aqueous wash liquid is then made up and contains 7.5 g/l of the ECE powder, 8.6 mmol/l of hydrogen peroxide and 5, 10 or 50 μmol of a compound of formula:

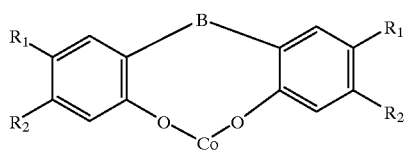
(108)

in which $R_1$, $R_2$ and B are as defined in the following Table.

Into 400 ml of the aqueous wash liquid (made up using town water of 12 degrees of hardness), there are placed 12.5 g. of test cotton fabric soiled with red wine, tea, coffee or blackberry stains, as well 37.5 g. of bleached cotton (i.e. giving a liquor ratio of 1:8).

The respective wash baths are each heated from 15° C. to the test temperature of 40° C. over a period of 10 minutes; and held at the test temperature for a further 10 minutes. The respective swatches are then rinsed under flowing, cold town water, spun dry and ironed.

The brightness value (Y) of the respective test swatches is then determined using an ICS SF 500 spectrophotometer. The value Y provides a measure of the level of bleach effect achieved. A difference of 1 Y unit is clearly detectable visually.

For reference purposes, the respective Y values are determined for each of the washed goods at 40° C. using peroxide alone (i.e. using no compound of formula 108).

The results obtained are set out in the following Table.

TABLE

| Example/ Compound | $R_a$ | $R_b$ | B | Bleach Effect ΔY at a concentration of | | |
|---|---|---|---|---|---|---|
| | | | | 5 μmol | 10 μmol | 50 μmol |
| control $H_2O_2$ only | | | | | <10 | |
| 8 (105) | $SO_3Na$ | H | CH=N(CH$_2$)$_2$N=CH | 15.0 | — | 20.6 |
| 9 (107) | $SO_3Na$ | H | CH=N(CH$_2$)$_4$N=CH | 12.7 | — | 17.1 |
| 10 (106) | $SO_3Na$ | H | CH=N(CH$_2$)$_3$N=CH | 10.0 | — | 16.2 |
| 11 (103) | $SO_3Na$ | H | CH=N—CH$_2$—(m-C$_6$H$_4$)—CH$_2$—N=CH | 14.6 | 17.9 | — |
| 12 | H | H | CH=N(CH$_2$)$_3$NH(CH$_2$)$_3$N=CH | 11.7 | — | 16.2 |
| 13 | H | H | CH$_2$NH(CH$_2$)$_2$NH(CH$_2$)$_2$NHCH$_2$ | 14.5 | — | 18.5 |
| 14 | H | H | NH—C(=O)—C(=O)—NH | 12.3 | — | 17.6 |
| 15 (101) | OH | H | CH=N—CH$_2$—(m-C$_6$H$_4$)—CH$_2$—N=CH | 15.1 | — | 19.1 |
| 16 (102) | $SO_3Na$ | H | CH=N—(m-C$_6$H$_4$)—N=CH | 15.2 | — | 20.3 |

TABLE-continued

| Example/Compound | $R_a$ | $R_b$ | B | Bleach Effect ΔY at a concentration of | | |
|---|---|---|---|---|---|---|
| | | | | 5 μmol | 10 μmol | 50 μmol |
| 17 (104) | $SO_3Na$ | H | 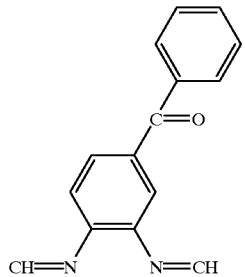 | 16.2 | — | 19.1 |

It is clear from the results in the Table that the bleaching improvement achieved with a fabric bleaching composition according to the invention significantly greater than that achieved using $H_2O_2$ alone.

EXAMPLES 18 and 19

Using the procedure described in Examples 8 to 17, tea-stained test cotton fabrics are washed at 40° C. for 30 minutes with an aqueous wash liquid containing 7.5 g/l of the ECE powder, 8.6 mmol/l of hydrogen peroxide and 50 μmol of a compound of formula (103) or (105), buffered to pH 10 with borax. In each case, the observed ΔY value is 20.

EXAMPLE 20

A machine dishwashing base powder is produced by mixing the following in the given proportions by weight:

15 parts trisodium citrate dihydrate;
6 parts copolymer of 1:4 maleic/acrylic acid of average mol. wt. 80,000;
9 parts amorphous sodium silicate ($Na_2O:SiO_2$ ratio 1:2);
20 parts anhydrous sodium carbonate;
9.1 parts anhydrous sodium percarbonate bleach;
2.2 parts of tetraacetyl ethylenediamine;
0.03 part of compound of formula (103);
0.04 part protease;
0.02 part of amylase;
1.7 parts of nonionic surfactant; and
1.4 parts of anhydrous sodium sulfate.

Soiled articles selected from crockery, glassware and cutlery are washed with an aqueous solution containing 3 g/l of the base powder at 55° C. and good soil removal is obtained.

What is claimed is:

1. A bleaching or washing composition comprising a) a peroxy compound; and
b) 0.0005 to 0.5%, by weight of cobalt, of one or more cobalt compounds having one of the formulae (1), (2), (3), (4), (5) or (6):

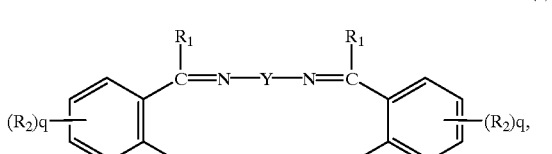
(1)

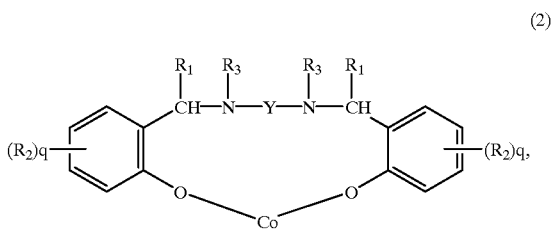
(2)

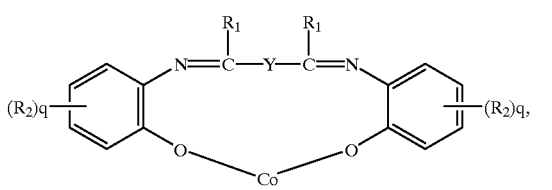
(3)

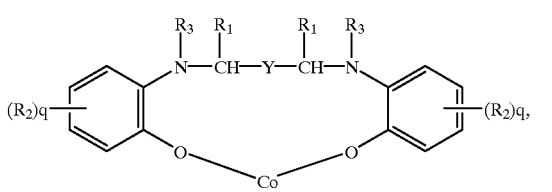
(4)

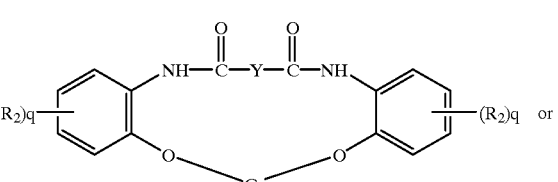
(5) or

-continued (6)

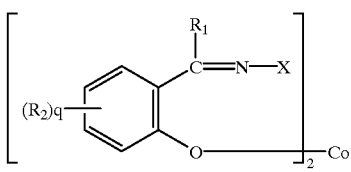

in which,

R₁ is hydrogen, alkyl, cycloalkyl or aryl;

R₃ is hydrogen or alkyl;

X is alkyl, —CH₂COOC₁–C₄alkyl, aryl, —NH-phenyl, hydroxy, amino or —NH—C(=O)—NH₂;

M is hydrogen, an alkali metal atom, ammonium or a cation formed from an amine; and q is 0, 1, 2 or 3, and in the compounds of the formulae (2), (3), (4), (5), and (6), R₂ is hydrogen, alkyl, alkoxy, halogen, cyano, NH(alkyl), N(alkyl)₂, N⁺(alkyl)₃, SO₃M, COOM or hydroxy, and Y is a direct bond, alkylene, cyclohexylene, o-, m- or p-phenylene, C(=O)—C(=O) or Y is a residue having one of the formulae:

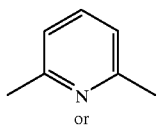

or

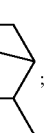

and in which, in the compounds of the formulae (1),

R₂ is alkyl, cyano, NH(alkyl), N(alkyl)₂, N⁺(alkyl)₃, SO₃M, COOM or hydroxy and

Y is a direct bond, cyclohexylene, o-, m- or p-phenylene, C₂–C₈-alkylene interrupted or substituted by NH, optionally substituted phenyl or o-, m- or p-phenylene, C(=O)—C(=O) or Y is a residue having one of the formulae:

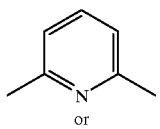

or

2. A composition according to claim 1 comprising
a) a peroxy compound; and
b) 0.005 to 0.05%, by weight of cobalt, of one or more cobalt compounds having one of the formulae (1) to (6).

3. A composition according to claim 1 in which a compound of formula (1) is present in which each R₁ is hydrogen, R₂ is OH or SO₃M in which M is as defined in claim 1, q is 1 and Y is C₂–C₈-alkylene interrupted by NH, C₂–C₈-alkylene interrupted or substituted by optionally substituted phenyl or o-, m- or p-phenylene, or Y is optionally substituted o-, m- or p-phenylene.

4. A composition according to claim 1 in which a compound of formula (2) or (4) is present in which each R₁ is hydrogen, R₂ is hydrogen, OH or SO₃M in which M is as defined in claim 1, R₃ is hydrogen, q is 0 or 1 and Y is C₂–C₈-alkylene interrupted by NH.

5. A composition according to claim 1 in which a compound of formula (3) is present in which each R₁ is hydrogen, R₂ is hydrogen, OH or SO₃M in which M is as defined in claim 1, q is 0 or 1 and Y is C₂–C₈-alkylene interrupted by NH.

6. A composition according to claim 1 in which a compound of formula (5) is present in which each R₂ is hydrogen, OH or SO₃M in which M is as defined in claim 1, q is 0 or 1 and Y is a direct bond.

7. A composition according to claim 1 in which a compound of formula (6) is present in which each R₁ is hydrogen, R₂ is hydrogen, OH or SO₃M in which M is as defined in claim 1, q is 1 and X is OH.

8. A composition according to claim 1 in which the peroxy component a) is hydrogen peroxide, a compound which liberates hydrogen peroxide, a peroxyacid, a peroxyacid bleach precursor or a mixture thereof.

9. A composition according to claim 8 in which the compound which liberates hydrogen peroxide is an alkali metal peroxide, -perborate, -percarbonate, -perphosphate or -persulfate; peroxylauric acid, peroxybenzoic acid, diperoxyisophthalic acid, 1,12-diperoxydodecanedioic acid or urea peroxide; or a mixture thereof.

10. A composition according to claim 9 in which the compound which liberates hydrogen peroxide is sodium percarbonate or sodium perborate.

11. A composition according to claim 8 in which the peroxyacid bleach precursor is a benz(4H)-1,3-oxazin-4-one derivative
2-(N,N,N-trimethyl ammonium)ethyl sodium-4-sulfophenyl carbonate chloride (SPCC)
N-octyl,N,N-dimethyl-N10-carbophenoxy decyl ammonium chloride (ODC)
3-(N,N,N-trimethyl ammonium)propyl sodium 4-sulfophenyl carboxylate
N,N,N-trimethyl ammonium toluyloxy benzene sulfonate
sodium-4-benzoyloxy benzene sulfonate (SBOBS)
N,N,N',N'-tetraacetyl ethylene diamine (TAED)
sodium-1-methyl-2-benzoyloxy benzene-4-sulfonate
sodium-4-methyl-3-benzoyloxy benzoate or
sodium nonanoyloxybenzene sulfonate (NOBS).

12. A composition according to claim 11 in which the peroxyacid bleach precursor is a substituted 2-phenyl-benz(4H)-1,3-oxazin-4-one, sodium nonanoyloxybenzene sulfonate or N,N,N',N'-tetraacetyl ethylene diamine.

13. A composition according to claim 1 in which the amount of the peroxy compound is 0.5 to 50% by weight, based on the total weight of the composition.

14. A fabric bleaching or washing composition according to claim 1 which also comprises a surfactant and a detergent builder.

15. A composition according to claim 14 comprising 5–50% of an anionic surfactant and/or a nonionic surfactant.

16. A composition according to claim 15 in which the anionic surfactant is a sulfate, sulfonate or carboxylate surfactant, or a mixture thereof.

17. A composition according to claim 15 in which the nonionic surfactant is a condensate of ethylene oxide with a C₉–C₁₅ primary alcohol having 3–8 moles of ethylene oxide per mole.

18. A composition according to claim 14 comprising 5–80% of a detergent builder.

19. A composition according to claim 18 comprising 10–60% of a detergent builder.

20. A composition according to claim 1 in which one or more agents capable of binding cobalt are present.

21. A composition according to claim 20 in which the agent capable of binding cobalt is an aminocarboxylate, an aminophosphonate, a polyamine or a mixture of these.

22. A composition according to claim 21 in which the agent capable of binding cobalt is diethylenetriaminepentamethylene phosphonic acid, diethylenetriaminepentaacetic acid, triethylenetetraaminehexaacetic acid or a salt thereof, or diethylenetriamine.

23. A composition according to claim 20 in which the agent capable of binding cobalt is present in an amount of 0.1 to 10%, based on the weight of the composition.

24. A dishwashing composition according to claim 1 which also contains a detergent builder component and a buffering agent.

25. A composition according to claim 18 in which the detergent builder is an alkali metal phosphate; a carbonate or bicarbonate; a silicate; an aluminosilicate; a polycarboxylate; a polycarboxylic acid; an organic phosphonate; an aminoalkylene poly(alkylene phosphonate); or a mixture of these.

26. A composition according to claim 1 in which a protease, cellulase, lipase, oxidase or amylase enzyme is present.

27. A composition according to claim 25 in which the detergent builder is sodium citrate, sodium carbonate, calcium carbonate, a zeolite or any mixture of these materials.

28. A composition according to claim 25 comprising 0.1 to 10% by weight of a low- to non-foaming nonionic surfactant.

29. A composition according claim 24 comprising 5 to 60% by weight of a detergent builder component; and 5 to 75% by weight of a buffering agent.

30. A composition according to claim 29 in which the buffering agent is an alkali metal carbonate, bicarbonate, borate or silicate.

31. A composition according to claim 30 in which the silicate is a sodium silicate having an $Na_2O:SiO_2$ ratio in the range of from 2:1 to 1:4.

32. A composition according to claim 1 comprising one or more of polymers known to be useful in preventing the transfer of labile dyes between fabrics during the washing cycle; fluorescent whitening agents; soil suspending agents; salts for adjusting the pH; foam regulators; anti-scale agents; clays which are effective in reducing spot formation on glassware; salts for adjusting the spray drying and granulating properties; perfumes; antistatic and softening agents; enzymes; photobleaching agents; pigments; and shading agents.

33. A composition according to claim 32 in which the polymer known to be useful in preventing the transfer of labile dyes beteween fabrics during the washing cycle is a polyvinyl pyrrolidone, optionally modified by the inclusion of an anionic or cationic substituent.

34. A composition according to claim 1 which is in powder or granulate form.

35. A composition according to claim 1 which is in liquid form and contains 0–5% water.

36. A process for the production of a composition as claimed in claim 34 in which a base powder is produced by spray-drying an aqueous slurry which contains all the components, apart from the components a) and b); then adding the components a) and b) by dry-blending them into the base powder.

37. A process for the production of a composition as claimed in claim 34 in which the component b) is added to an aqueous slurry containing the surfactant and builder components, followed by spray-drying the slurry prior to dry-blending component a) into the mixture.

38. A process for the production of a composition as claimed in claim 34 in which a nonionic surfactant component is not present, or is only partly present in an aqueous slurry containing anionic surfactant and builder components; component b) is incorporated into the nonionic surfactant component, which is then added to the spray-dried base powder; and finally component a) is dry-blended into the mixture.

39. A bleaching or washing process comprising contacting a fabric or dishes to be bleached or washed with an effective amount of a bleaching or washing composition according to claim 1.

40. A process according to claim 39 in which the amount of the bleaching or washing composition used is such that the amount of cobalt complex b) provides from 0.001 to 100 ppm of cobalt in the bleaching or washing bath.

41. A composition according to claim 13 in which the amount of the peroxy compound is 2 to 20% by weight, based on the total weight of the composition.

42. A composition according to claim 15 comprising 5–25% of an anionic surfactant and/or a nonionic surfactant.

43. A composition according to claim 28 comprising 0.5 to 5% by weight of a low- to non-foaming nonionic surfactant.

44. A process according to claim 40 in which the amount of the bleaching or washing composition used is such that the amount of cobalt complex b) provides from 0.01 to 20 ppm of cobalt in the bleaching or washing bath.

* * * * *